United States Patent
Hardy et al.

(10) Patent No.: US 9,370,451 B2
(45) Date of Patent: Jun. 21, 2016

(54) MEDICAL DEVICE

(75) Inventors: Craig Julian Hardy, Cheshire (GB);
Stewart Andrew Darby, Staffordshire (GB); Andrew Guy Eason, Cheshire (GB)

(73) Assignee: MEDTRADE PRODUCTS LIMITED, Cheshire (GB)

( * ) Notice: Subject to any disclaimer, the term of this patent is extended or adjusted under 35 U.S.C. 154(b) by 1371 days.

(21) Appl. No.: 12/515,282

(22) PCT Filed: Nov. 16, 2007

(86) PCT No.: PCT/GB2007/004382
§ 371 (c)(1),
(2), (4) Date: Dec. 1, 2009

(87) PCT Pub. No.: WO2008/059266
PCT Pub. Date: May 22, 2008

(65) Prior Publication Data
US 2010/0092525 A1    Apr. 15, 2010

(30) Foreign Application Priority Data

Nov. 17, 2006 (GB) .................................. 0622970.2

(51) Int. Cl.
*A61F 13/15* (2006.01)
*A61L 15/44* (2006.01)
*A61L 15/62* (2006.01)
*A61F 13/00* (2006.01)

(52) U.S. Cl.
CPC .......... *A61F 13/15211* (2013.01); *A61L 15/44* (2013.01); *A61L 15/62* (2013.01); *A61F 2013/00906* (2013.01); *A61L 2300/418* (2013.01); *A61L 2300/622* (2013.01)

(58) Field of Classification Search
CPC ............................................. A61F 2013/00931
See application file for complete search history.

(56) References Cited

U.S. PATENT DOCUMENTS

| | | | |
|---|---|---|---|
| 4,790,836 A | | 12/1988 | Brecher |
| 4,921,949 A | * | 5/1990 | Lang et al. ...................... 536/20 |
| 5,691,015 A | * | 11/1997 | Tsukamoto et al. .......... 428/35.2 |
| 6,033,769 A | | 3/2000 | Brueggemann et al. |
| 6,657,004 B2 | * | 12/2003 | Mizutani ......................... 525/57 |
| 2006/0173492 A1 | * | 8/2006 | Akerfeldt et al. .............. 606/232 |

FOREIGN PATENT DOCUMENTS

| | | |
|---|---|---|
| GB | 1329693 | 9/1973 |
| WO | 9405341 | 3/1994 |
| WO | 2008059266 A2 | 5/2008 |

* cited by examiner

*Primary Examiner* — Benjamin Packard
(74) *Attorney, Agent, or Firm* — Barlow, Josephs & Holmes, Ltd.

(57) ABSTRACT

A medical device for delivery of a therapeutic agent to a physiological target site includes a flexible receptacle containing said therapeutic agent, wherein at least a part of the receptacle is formed of a water-soluble or water-dispersible material. The therapeutic agent may include a haemostatic agent and the physiological target site may be a wound.

56 Claims, 1 Drawing Sheet

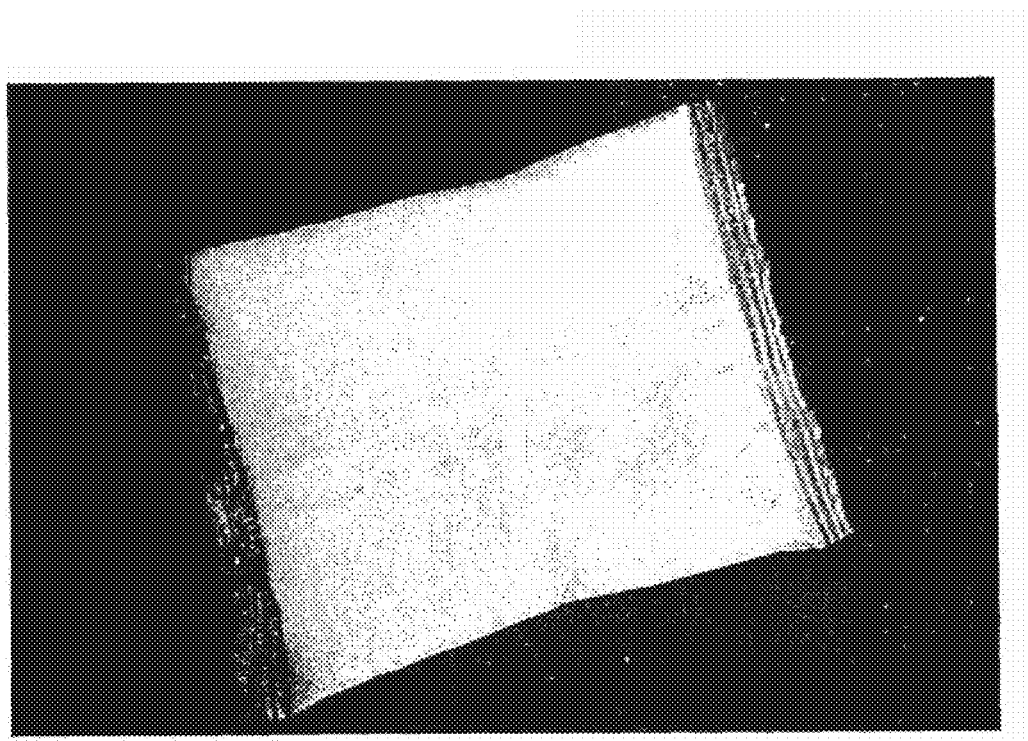

MEDICAL DEVICE

The present invention relates to a medical device for delivery of a therapeutic agent to a physiological target site.

There are many circumstances in which animals, both human and non-human, may become injured or wounded leading to bleeding. In the case of minor wounds, the bleeding may be stemmed by the natural haemostatic mechanisms of the body, which lead to coagulation of the blood to form solid clots which stop haemorrhage and aid repair of damaged blood vessels. Basic first aid may be administered in some cases to stem blood flow and assist wound healing.

In the case of more severe wounds, however, blood loss may be considerable. In the absence of medical intervention to stem blood flow from a severe wound, there is a significant risk of death. Severe traumatic wounds may occur in a variety of situations, for example following road traffic accidents, or on the battlefield. Surgical wounds may also lead to significant loss of blood.

In an attempt to address the problem of blood loss from wounds, particularly in traumatic situations in which medical care is unavailable or inadequate, haemostatic products have been developed which facilitate stemming of blood flow.

Haemostatic agents are typically presented in the form of solid powders or granules, or as liquids. All of these forms, being flowable, provide for good contact with the irregular surfaces typical of wounds so that good haemostasis may be achieved. However, the flowable nature of the particulate or liquid haemostatic agents also renders them relatively difficult to handle in use. It can be a problem retaining the flowable haemostatic agent at the wound site where the stemming of blood flow is required.

In an alternative form, haemostatic agents are presented as solid sheet materials. The haemostatic agents in this form are generally easier to handle and apply to the wound site, but a drawback is that they conform less well than the flowable haemostatic agents to the irregular surfaces and crevices typical of wounds. As such, haemostatic efficacy may be compromised.

An example of a haemostatic agent presented in particulate form is 'QuikClot'®, a zeolite compound which absorbs water from blood flowing from a wound to concentrate the clotting factors present in the blood, such that the blood coagulates more quickly. In a development of this product, a gauze bag is provided in which the haemostatic agent is contained. Whilst this improves the ease of handling and application of the haemostat, the gauze bag physically separates the haemostat from the body tissues and blood at the wound site. This may reduce the efficacy of the haemostat. Further, although the gauze bag is flexible, the particles of haemostatic agent are unable to move outside the bag and into any crevices or irregular surfaces of the wound, as the holes in the gauze bag are smaller than the typical particle size of the haemostatic agent retained in the gauze bag. The gauze bag remains in situ until removed.

The present invention has been made from a consideration of the aforementioned problems.

According to a first aspect of the present invention there is provided a medical device for delivery of a therapeutic agent to a physiological target site, said device comprising a flexible receptacle containing said therapeutic agent, wherein at least a part of the receptacle is formed of a water-soluble or water-dispersible material.

In use, the device is placed at or in a physiological target site whereupon it comes into contact with body fluid(s). This brings about dissolution or breaking up of the receptacle or water-soluble or water-dispersible part thereof, such that the therapeutic agent is exposed or released from containment within the receptacle at the physiological site. In presently preferred embodiments, the therapeutic agent comprises a haemostatic agent and the physiological site is a wound. It will be appreciated, however, that the invention may have broad application for delivery of a range of therapeutic agents to different body sites.

Advantageously, the medical device according to this aspect of the present invention is easy to handle and apply. The device is stored dry prior to application and then in use the receptacle at least partially dissolves or breaks up upon contact with body fluid(s) when the device is applied to the target site. The medical device may be provided with appropriate packaging to maintain dryness prior to use.

The therapeutic agent may take any form. The therapeutic agent typically comprises a flexible material. For instance, the therapeutic agent may be a particulate material, such as a powder or granular material, a liquid, solution, gel, emulsion, foam, or fibrous material.

In some preferred embodiments, the therapeutic agent is flowable. Thus, in use, when the device is placed at or in the target body site, the receptacle at least partially dissolves or breaks up upon contact with body fluid(s) and the therapeutic agent is released from containment to flow from the device and into the surrounding site.

Where the therapeutic agent comprises a flowable haemostatic agent, said haemostatic agent may be delivered by the device to a wound site whereupon it is released, as at least part of the receptacle is dissolved or broken up by blood, tissue fluid and other body fluids, to flow across irregular wound surfaces and into any crevices. As such, the present invention may provide a haemostatic product having the beneficial properties of the flowable haemostatic agents known in the art and also the ease of handling and application more associated with the haemostatic sheet materials known in the art.

By "water-soluble material" it is meant any material which dissolves in water or an aqueous liquid. By "water dispersible material" it is meant any material which breaks up and disperses in water or an aqueous liquid. These terms are not mutually exclusive.

In certain circumstances, it may be desirable or necessary that the therapeutic agent is non-aqueous, to avoid unwanted dissolution or breaking up of the receptacle or water-soluble part there of prior to use. However, it is possible to use a portion of water in the therapeutic agent, provided that the receptacle is not dissolved or dispersed by said therapeutic agent. For example, a therapeutic agent comprising a liquid component of around 20% water and around 80% ethanol is contained effectively within a receptacle formed from polyvinyl alcohol. Other examples will be apparent to a person skilled in the art.

Upon application, the receptacle may adhere to the surrounding tissues at the target site upon contact with surfaces wet with water or body fluid(s). Usefully, this helps to retain the device in place at the target site. Thus, the receptacle is preferably formed, at least in part, from a material which adheres to wet surfaces. This may be the water-soluble or water-dispersible material, which may adhere to surfaces at the target site as it begins to dissolve or break down. Suitable materials include polymeric materials as described herein. Advantageously, in the case of a haemostatic medical device according to the present invention, as the receptacle adheres to a wound site it acts as a physical barrier to help reduce or eliminate blood flow from the wound until the haemostatic agent contained within the receptacle is exposed or released.

The physiological target site may be any site in or on the body of an animal. The animal may be a human or non-human animal. The physiological target site may be a wound.

The receptacle may take any suitable form and may be provided in a range of different sizes, shapes and thicknesses. For example, the receptacle may be a generally flat shape with little height relative to its width/depth. Any regular or irregular shape may be employed. The receptacle may be, for instance, generally square, rectangular, circular or elliptical. The receptacle may alternatively comprise a shape having more significant height. Again, any regular or irregular shape may be employed. By way of example, the receptacle may comprise a tube, sphere, cone, cube, pyramid, or 'horse shoe', or any other three-dimensional form. The receptacle may comprise a torus, or doughnut shape, which facilitates placement of the device around another object. The receptacle may have a projection or protrusion for placement within any hole, cavity or orifice.

A range of different thicknesses of the receptacle may be employed. For example, the receptacle may have a thickness of between around 10 μm and around 100 μm, although materials having thicknesses outside these limits may readily be used.

With regard to the size of the device, it will be appreciated that a wide range of different sizes are encompassed by the present invention. By way of example only, this aspect of the present invention may provide a device of between around 1 g and around 100 g.

The receptacle may be formed of any suitable flexible materials. It will be appreciated that biocompatible materials of low toxicity are generally preferred. By way of example, the receptacle may be formed from a film or foam material. The receptacle may be plain or at least partially patterned and may optionally be apertured. It will be understood that where the receptacle is provided with apertures, these should generally be small enough to prevent significant loss of the therapeutic agent therethrough. Where the therapeutic agent is in the form of a particulate solid, for instance, any apertures in the receptacle should be of smaller size than the size of the particles of the therapeutic agent. By way of example, the therapeutic agent may have a particle size in the range of from about 1 μm to about 500 μm. Also by way of example, the aperture size of the receptacle may vary between 0 to about 300 μm, depending upon the particle size.

The receptacle at least in part comprises a water-soluble or water-dispersible material. The receptacle may be formed of a combination of at least one water-soluble or water-dispersible material with at least one further material which is neither water-soluble nor water-dispersible. Such a combination provides for a receptacle which exposes or releases its contents when the water-soluble or water-dispersible material(s) come into contact with water or body fluid(s) but retains some structural integrity by virtue of the material(s) which are not dissolved or dispersed in the water or body fluid(s). Different arrangements may be provided of the water-soluble or water-dispersible material(s) on the one hand and the non-water-soluble and non-water-dispersible material(s) on the other hand. For instance, the receptacle may be formed from a fabric or other material comprising a combination of at least one water-soluble or water-dispersible material with at least one further material which is neither water-soluble nor water-dispersible. The receptacle may be formed having soluble and insoluble regions, of at least one water-soluble or water-dispersible material, and at least one material which is neither water-soluble nor water-dispersible, respectively. A combination of a water-soluble or water-dispersible film or other sheet with a film or other sheet which is neither water-soluble nor water-dispersible may be used. These examples are not exhaustive.

Alternatively, the receptacle may be substantially completely water-soluble or water-dispersible. Advantageously, complete dissolution or breakdown of the receptacle may avoid the need for removal of any materials from the physiological site following application of the medical device and delivery of the therapeutic agent. Thus, the receptacle may be made from material(s) which are metabolised within the body. Examples of such materials include any of the following, alone or in any combination: collagen, oxidised regenerated cellulose, poly lactic acid, poly glycolic acid, chitin, chitosan, gelatine, hyaluronic acid. This list is non-exhaustive.

The rate at which the water-soluble or water-dispersible material(s) of the receptacle dissolve or disperse can vary within the terms of the present invention. The greater the rate of dissolution or dispersal of the material(s), the greater the rate at which the therapeutic agent is exposed or released upon contact with water or body fluid(s) to bring about the desired therapeutic effect. In some circumstances, it may be desirable to have a short lag period before exposure or release of the therapeutic agent following contact of the device with water or aqueous fluid(s), to allow handling time for positioning and if necessary re-positioning of the device at the target site. The properties of the receptacle may be varied by selecting different water-soluble or water-dispersible material(s) and/or different combinations thereof. Thus, material(s) or combinations thereof may be selected according to the desired rate of dissolution or dispersal, temperature sensitivity, pH sensitivity, etc. The thickness of the receptacle may also be varied to adjust the rate of release or exposure of the contained therapeutic agent. Such selections will be within the normal understanding and capability of the skilled person.

It will be appreciated that the rate of dissolution or dispersal may vary with the temperature at the target site. The water-soluble or water-dispersible material(s) may be susceptible to dissolution or dispersal at temperatures of around 0 to around 100° C., such as around 45° C. or below, more preferably around 41° C. or below and most preferably around 37° C. or below.

By way of illustration only, it may be desirable that at body temperature the water-soluble or water-dispersible material(s) begin to dissolve or disperse within around 1 second to around 120 seconds of exposure to water or aqueous fluid(s), such as within around 5 to around 120 seconds, preferably within around 60 seconds, and most preferably within around 30 seconds. Substantially complete dissolution or dispersal of the material(s) may occur within around 1 second to around 30 minutes, such as within around 5 minutes, preferably within around 3 minutes, and most preferably within around 2 minutes.

Other factors may affect the dissolution or dispersal of the water-soluble or water-dispersible material(s) of the receptacle, such as the pH at the target site.

The receptacle may be formed from any sheet, apertured sheet, foamed sheet, capsule, blister, fabric or net material, or any other material capable of containing the therapeutic agent, particularly the haemostats described herein. The receptacle may be formed from a sheet material folded and sealed to provide for containment of the therapeutic agent. Thus, the receptacle may comprise a bag, pouch, sachet, or the like.

Methods and apparatus for production and filling of receptacles of this type are known. For example, the medical device according to this aspect of the present invention may be manufactured using methods and apparatus already known for use in the food industry for making and filling bags, sachets, pouches, capsules, and the like, for instance tea bags. Certain modifications to existing methods and apparatus may be desirable or necessary, although any modifications will be within the normal capability of the skilled person. For example, it may be desirable to carry out the manufacture of the medical device according to this aspect of the present invention in an environment of controlled moisture and/or temperature, to ensure consistent quality and integrity of the water-soluble or water-dispersible receptacle.

The receptacle may comprise a water-soluble or water-dispersible polymeric material. Non-limiting examples of suitable polymeric materials include any of the following, either alone or combination: cellulose, cellulose derivatives, such as hydroxy propyl methyl cellulose, hydroxyl propyl cellulose, carboxy methyl cellulose, ethyl cellulose, hydroxyl ethyl cellulose, oxidised cellulose, polyvinyl alcohol, polyvinyl pyrrolidone, pectins, chitosans, alginates, including sodium alginate and propylene glycol alginate, polysaccharides, gelatins; carrageenans, polyethylene glycol, natural gums including xanthan gum, tragacantha, guar gum, acacia gum, arabic gum, water-dispersible polyacrylates including polyacrylic acid, methylmethacrylate copolymer, carboxyvinyl copolymers, superabsorbents, polylactic acid, polyurethane, poly glycolic acid, hyaluronic acid.

The dissolution or dispersion of one or more materials used to form the receptacle may be pH dependant, providing for a device which has a pH-sensitive dissolution or dispersion rate. This may be used to keep the receptacle from dissolving or dispersing until introduced to the body.

The material(s) forming the receptacle may also contain one or more of the following in any combination: plasticising agents (such as glycerol, propylene glycol, polyethylene glycol), insolublising agents, solublising agents, surfactants, dispersed insoluble materials, dispersion adding materials, casting aids, bonding aids, adhesives, materials which render the receptacle susceptible to dispersion upon exposure to photochemical, ultraviolet, biological, or chemical sources.

Where non-water-soluble materials are also present, these may comprise, for example, one or more of the following in any combination: cellulose, chitin, silica, water insoluble cellulose derivatives, calcium alginate, zeolite, sand, chalk, water-swellable compounds, polymeric materials such as polyurethane or polyisobutylene. This list is not exhaustive.

Usefully, the receptacle may itself be therapeutically active. For instance, the receptacle may comprise a therapeutic agent or other active component. The therapeutic agent or other active component may be incorporated in the material from which the receptacle is formed and/or added thereto.

The receptacle may itself be haemostatic. A haemostatic agent may be incorporated in the material from which the receptacle is formed and/or added thereto. Advantageously, in use of the device haemostasis may be initiated even before the contents of the receptacle have been exposed or released by dissolution or dispersal of the receptacle or part thereof.

In some preferred embodiments, the receptacle is formed from a water-soluble or water-dispersible film. Suitable films are available from Soluble Technology Ltd., MonoSol, LLC, AMC (UK) Ltd., Nippon Goshei (e.g. Hi-Selon®; Gohensol®), Adhesives Research Inc., Dalian BHY Inc., and Rapid Dissolve Technologies. Water soluble papers, such as Dissolvo® (Dissolvo LLC), may also be employed.

The medical device may be provided sterile or non-sterile. Where the device is provided sterile, sterilisation may be carried out using any of the known methods, such as gamma irradiation, electron beam treatment, heat treatment, etc. A non-sterile device may be provided in combination with one or more preservatives.

According to a further aspect of the present invention there is provided a method of manufacturing a medical device for delivery of a therapeutic agent to a physiological target site, said method comprising the steps of introducing the therapeutic agent into a flexible receptacle, at least a part of said receptacle being formed of a water-soluble or water-dispersible material, and containing the therapeutic agent within the receptacle.

The receptacle may be made from any pre-formed tube, sock, bag, sachet, pouch, wallet, or the like, closed or sealed as necessary along any side or sides.

Alternatively, roll stock, flat roll stock or sheet material may be formed into a tube, sock, bag, sachet, pouch, wallet, or the like and closed or sealed as necessary along any side or sides.

Additionally, any combinations of roll stock, flat roll stock or sheet material and/or preformed tubes, socks, bags, sachets, pouches, wallets, or the like may be used, closed or sealed as necessary along any side or sides.

Any of the known manual or automated methods and apparatus may be used to manufacture the medical device. For example, a film or other sheet material may be longitudinally sealed to form a tube which is filled with the therapeutic agent and transversely sealed at both ends to contain said therapeutic agent. The tube may be sealed at a first end before introduction of the therapeutic agent and subsequent sealing at a second end to contain the therapeutic agent. Sealing may be effected, for example, by any of the following either alone or in combination: heat, pressure, ultrasonics, moisture, glue or other adhesive. The manner of sealing may be chosen according to the nature of the film or other sheet material.

According to a further aspect of the present invention there is provided the use of a medical device comprising a flexible receptacle containing a therapeutic agent, wherein at least a part of the receptacle is formed of a water-soluble or water-dispersible material, for delivery of a therapeutic agent to a physiological target site.

In preferred embodiments, the medical device comprises a haemostatic device and, as such, the therapeutic agent comprises at least one haemostatic agent. Any suitable haemostatic agent may be employed.

In some embodiments, the haemostatic agent is chitosan-based. The chitosan-based haemostat may comprise a powder of a chitosan salt. Chitosan is a derivative of solid waste from shell fish processing and can be extracted from fungus culture. Chitosan is a water-insoluble cationic polymeric material. For use with the present invention, therefore, the chitosan is first converted into a water-soluble salt. Being water-soluble, the chitosan salt is soluble in blood to form a gel which stems blood flow.

Chitosan salts are ideally suited for use in the present invention as chitosan is readily broken down in the body. Chitosan is converted to glucosamine by the enzyme lysosyme and is therefore excreted from the body naturally. It is not necessary to remove chitosan from the body. Furthermore, chitosan salts exhibit mild antibacterial properties and as such their use reduces the risk of infection.

Chitosan salts suitable for use with the present invention include any of the following either alone or in combination: acetate, lactate, succinnate, malate, sulphate, acrylate. These salts are disclosed by way of example only, and do not limit the type of chitosan salt which may be employed within the terms of the present invention. One preferred chitosan salt is chitosan succinnate.

The chitosan salt is prepared by combining chitosan with the appropriate acid. The acid may be any inorganic or organic acid which yields a soluble chitosan salt. For example, chitosan phosphate is insoluble and so phosphoric acid is unsuitable.

The chitosan salt preferably constitutes at least around 5% by weight of the haemostatic powder, more preferably at least around 20% by weight of the powder.

The chitosan salt may have a particle size such that it will pass through a 5 mesh screen but be retained by a 80 mesh screen. Preferably, the chitosan salt has a particle size such that it will pass through a 20 mesh screen but be retained by a 50 mesh screen. The desired particle size may be achieved by grinding the chitosan salt and sorting by any suitable means, for example sieving. Such sizing processes are well known to those skilled in the art and will not be described further.

Surprisingly, it has been found that by adding at least one inert material to the chitosan salt the performance of the haemostatic powder is enhanced. The inert material may comprise any material which does not gel quickly, for example a material which gels in greater than around 30 seconds to around 1 minute of application to a bleeding wound. Suitable inert materials include, but are not limited to, any of the following either alone or in combination: cellulose, fumed silica, sand, clay, alginate, micro crystalline cellulose, oxidised regenerated cellulose, polyethylglycol, guar gum, xanthan gum, chitosan, chitosan derivatives, chitin, sucrose, lactose, pectin, carboxy methyl cellulose, ground corn meal, collagen, gelataine, poly vinyl alcohol, acrylic acid, Carbopol® polymers (poly acrylic acid polymers), barium sulphate, clay, lactose, sucrose, starch. Ideally, the inert material will have a known metabolic pathway in order that the body can degrade of and dispose of said material if the haemostatic powder remains in situ.

The inert material(s) may constitute from at least around 30% by weight of the haemostatic powder.

Preferably, the particle size of the inert material at least approximates to that of the chitosan salt.

Advantageously, the presence of an inert material gives rise to excellent wetting out properties.

It has further been found that by adding at least one medical surfactant to the haemostatic powder the performance of the powder is enhanced. Accordingly, the haemostatic powder may also comprise at least one medical surfactant. Suitable medical surfactants include any of the following either alone or in combination: BASF Pluronics® (block copolymers based on ethylene oxide and propylene oxide), lauric acid, oleic acid, other fatty acids and fatty acid salts, silicone based surfactants and emulsifiers.

Where present, the medical surfactant preferably constitutes from around 0.001% to around 10% by weight of the total haemostatic powder composition, more preferably from around 0.5% to 1%.

The surfactant may be dissolved during manufacturing such that said surfactant forms a coating around the particles of the powder. Alternatively, the surfactant may be added in the form of a solid.

The chitosan-based haemostatic powder preferably has a pH of from around 3.5 to around 6.

One method of manufacture of the chitosan-based haemostatic material involves preparation of an active base material by preparing a mixture of chitosan and acid in a solvent in which the chitosan is insoluble (usually 80:20 ethanol:water). Where used, a surfactant may also be added to this mixture. The solvent is evaporated to provide a substantially dry active base material. The active base material may then optionally be combined with other materials such as inert materials to provide the haemostatic powder.

Thus, the chitosan-based haemostat may comprise a powder of a chitosan salt, optionally in combination with an inert material and/or a medical surfactant.

An example of a suitable commercially available chitosan-based haemostat is Celox™ (MedTrade Products Limited).

Other non-limiting examples of haemostatic agents suitable for use in the present application include QuikClot®, and TraumaDEX™, a starch-based haemostat. Still further haemostatic agents include collagen powders, gelatin powders, superabsorbents, acrylic-based polymers, cationic materials, oxidised regenerated cellulose, alginate, Factor VIII, thrombin, fibrinogen, calcium, and vitamin K. Other suitable haemostatic agents will be known to those skilled in the art. The haemostatic agents may be used alone or in any combination.

The haemostatic agent may include one or more water-swellable materials which swell upon contact with water or aqueous fluids. In use, when the receptacle is initially breached by dissolution or breakdown of the water-soluble or water-dispersible material, the ingress of water or aqueous body fluid(s) into the receptacle brings about a swelling of the water-swellable material(s). This in turn expands the receptacle from the inside and accelerates the breaking up and dissolution or dispersal of the receptacle. By way of example, superabsorbent materials of the type known in the art provide suitable water-swellable materials. These materials include carboxymethylcellulose superabsorbents and chitosan super absorbents, for instance.

A further aspect of the present invention comprises a haemostatic device for delivery of a haemostatic agent to a physiological target site, comprising a flexible receptacle containing said haemostatic agent, wherein at least a part of the receptacle is formed of a water-soluble or water-dispersible material.

The present invention will now be described further by way of example only with reference to the following examples and the accompanying drawings, in which:

FIG. 1 shows a representative medical device according to an aspect of the present invention.

Example 1

A medical device of the invention was manufactured using a sachet making machine (JDA Progress). Celox™ chitosan-based haemostat (15 g) was sealed in an apertured bag made from a 30 μm poly vinyl alcohol film, grade EF220 (Soluble Technology Ltd.). The longitudinal edges of the soluble film (provided in a roll) were first heat sealed to each other to provide a hollow tube. A first transverse heat seal was applied across the tube and the haemostat was added to the tube from above the first transverse heat seal. Finally, a second transverse heat seal was applied above the haemostat at the opposite end from the first transverse heat seal. The resulting bag containing the haemostat was cut from the tube of film.

The medical device is shown in FIG. 1. The receptacle comprises a bag of the PVA film, with a longitudinal seal extending generally centrally along a first side of the bag. The bag is transversely sealed at its first and second ends. The haemostat is contained effectively within the bag.

A large glass container was filled with water. The bag was pushed under the surface of the water and into a corner of the container. This was designed to simulate a wound site or bleeding point. Almost immediately, the bag stuck to the surface of the glass container and held in place.

The film started to break up within around 10 seconds and the haemostat started to be released.

By around 1 minute, the bag was substantially dispersed or broken up and the majority of the haemostat was released.

Example 2

A medical device was produced in accordance with Example 1.

The device was tested in a glass container filled with saline. Again, the bag was pushed under the surface of the liquid and into a corner. The bag stuck to the glass, holding itself in place.

The film started to break up within around 30 seconds.

By around 2 minutes, the bag was substantially dispersed or broken up and the majority of the haemostat released.

Example 3

The haemostatic granules were removed from a Quik-Clot® ACS product (Z-Medica Corporation) and half of them filled and sealed into an apertured bag made from a 30 μm poly vinyl alcohol film, grade EF220 (Soluble Technology Ltd.), using a laboratory heat sealing bar.

A large glass container was filled with saline. The bag was pushed under the surface of the water and into a corner of the container. This was designed to simulate a wound site or bleeding point. Almost immediately, the bag stuck to the surface of the glass container and held in place.

Again, the film started to break up within around 30 seconds and the haemostat started to be released.

By around 2 minutes, the bag was substantially dispersed or broken up and the majority of the haemostat was released.

Example 4

Celox™ chitosan-based haemostat (10 g) was sealed into a bag formed from a fabric of soluble acidified chitosan fibres. The bag was made using a laboratory heat sealing bar, a 20 μm PVA film being placed between the chitosan fabric layers before applying heat and pressure to bring about sealing.

A large glass container was filled with saline. The bag was pushed under the surface of the water and into a corner of the container. The bag held in place.

The bag started to break up within around 45 seconds and the haemostat started to be released.

By around 2 minutes, the bag material had swollen, become weak and broken up and the majority of the haemostat was released.

Example 5

Celox™ chitosan-based haemostat (15 g) was sealed in an apertured bag made from two separate films bonded at their edges using a laboratory heat sealing bar with adjustable temperature. A first side of the bag was formed from a soluble 30 μm PVA film, grade EF220 (Soluble Technology Ltd.). The second side of the bag was formed from an insoluble 25 μm polyurethane film (Intellicoat Ltd.).

A large glass container was filled with saline. The bag was pushed under the surface of the water and into a corner of the container. The soluble film of the first side of the bag was placed downwards and towards the corner of the container, the insoluble polyurethane film on the second side of the bag facing upwards. Almost immediately, the bag stuck to the surface of the glass container and held in place.

The PVA film started to break up within around 45 seconds and the haemostat started to be released from the bag.

By around 3 minutes, the PVA side of the bag was substantially dispersed or broken up and the majority of the haemostat was released. The polyurethane side remained in one piece and could be removed at any convenient time.

It is of course to be understood that the present invention is not intended to be restricted to the details of the foregoing embodiments, which are described by way of example only.

The invention claimed is:

1. A haemostatic medical device for topical delivery of a haemostatic agent to a physiological wound site, said device comprising:
    a flowable haemostatic agent; and
    a flexible receptacle, the flexible receptacle having a configuration selected from the group consisting of a bag, a pouch, and a sachet, the flexible receptacle having an outer wall which is configured and arranged to overlie the physiological wound site, conform to a contour of the physiological wound site and make contact with bodily fluids, water or aqueous fluids present at the physiological wound site,
    wherein at least a portion of the outer wall of the flexible receptacle is formed of a water-soluble or water-dispersible material, and
    wherein the flowable haemostatic agent is contained within an interior of the flexible receptacle, and
    wherein said flowable haemostatic agent is capable of being delivered to the physiological wound site upon the dissolution or dispersion of the outer wall as a result of contact with the bodily fluids, water or aqueous fluids.

2. A haemostatic medical device according to claim 1, wherein the receptacle is completely water-soluble or water-dispersible.

3. A haemostatic medical device according to claim 1, wherein the water-soluble or water-dispersible material is susceptible to dissolution or dispersal at temperatures of around 45° C. or below.

4. A haemostatic medical device according to claim 3, wherein the water-soluble or water-dispersible material is susceptible to dissolution or dispersal at temperatures of around 41° C. or below.

5. A haemostatic medical device according to claim 4, wherein the water-soluble or water-dispersible material is susceptible to dissolution or dispersal at temperatures of around 37° C. or below.

6. A haemostatic medical device according to claim 1, wherein at body temperature the water-soluble or water-dispersible material begins to dissolve or disperse within around 1 second to around 120 seconds of exposure to bodily fluids, water or aqueous fluid(s).

7. A haemostatic medical device according to claim 6, wherein at body temperature the water-soluble or water-dispersible material begins to dissolve or disperse within around 5 seconds to around 120 seconds of exposure to bodily fluids, water or aqueous fluid(s).

8. A haemostatic medical device according to claim 7, wherein at body temperature the water-soluble or water-dispersible material begins to dissolve or disperse within around 60 seconds of exposure to bodily fluids, water or aqueous fluid(s).

9. A haemostatic medical device according to claim 8, wherein at body temperature the water-soluble or water-dispersible material begins to dissolve or disperse within around 30 seconds of exposure to bodily fluids, water or aqueous fluid(s).

10. A haemostatic medical device according to claim 1, wherein at body temperature substantially complete dissolution or dispersal of the water-soluble or water dispersible material occurs within around 1 second to around 30 minutes of exposure to bodily fluids, water or aqueous fluid(s).

11. A haemostatic medical device according to claim 10, wherein at body temperature substantially complete dissolution or dispersal of the water-soluble or water-dispersible material occurs within around 5 minutes of exposure to bodily fluids, water or aqueous fluid(s).

12. A haemostatic medical device according to claim 11, wherein at body temperature substantially complete dissolution or dispersal of the water-soluble or water-dispersible material occurs within around 2 minutes of exposure to bodily fluids, water or aqueous fluid(s).

13. A haemostatic medical device according to claim 1, wherein the receptacle is formed from a combination of at least one water-soluble or water-dispersible material with at least one further material which is neither water-soluble nor water-dispersible.

14. A haemostatic medical device according to claim 13, wherein the receptacle is formed from a fabric comprising a combination of at least one water-soluble or water-dispersible material with at least one further material which is neither water-soluble nor water-dispersible.

15. A haemostatic medical device according to claim 13, wherein the receptacle has at least one soluble region formed of the at least one water-soluble or water-dispersible material, and at least one insoluble region formed of the at least one material which is neither water-soluble nor water-dispersible.

16. A haemostatic medical device according to claim 13, wherein the receptacle is formed from a material comprising a sheet of a water-soluble or water-dispersible material together with a sheet of a material which is neither water-soluble nor water-dispersible.

17. A haemostatic medical device according to claim 1, wherein the receptacle is formed from a sheet material folded and sealed to provide for containment of the haemostatic agent.

18. A haemostatic medical device according to claim 1, wherein the receptacle is formed from a material selected from a film, foam, fabric or net material.

19. A haemostatic medical device according to claim 1, wherein the water-soluble or water-dispersible material comprises a polymeric material.

20. A haemostatic medical device according to claim 19, wherein the polymeric material comprises any of the following, either alone or combination: cellulose; cellulose derivatives; polyvinyl alcohol; polyvinyl pyrrolidone; pectins; chitosans; alginates; polysaccharides; gelatins; carrageenans; polyethylene glycol; natural gums; water-dispersible polyacrylates, including polyacrylic acid; methylmethacrylate copolymer; carboxyvinyl copolymers; superabsorbents; polylactic acid; polyurethane; poly glycolic acid; and hyaluronic acid.

21. A haemostatic medical device according to claim 13, wherein the receptacle is formed from a material comprising one or more of the following in any combination: plasticising agents; insolublising agents; solublising agents; surfactants; dispersed insoluble materials; dispersion adding materials; casting aids; bonding aids; adhesives; materials which render the receptacle susceptible to dispersion upon exposure to photochemical, ultraviolet, biological, or chemical sources.

22. A haemostatic medical device according to claim 21, wherein the insoluble materials comprise one or more of the following in any combination: cellulose, chitin, silica, water insoluble cellulose derivatives, calcium alginate, zeolite, sand, chalk, water-swellable compounds, polymeric materials.

23. A haemostatic medical device according to claim 1, wherein the receptacle is formed from a material susceptible to metabolisation within the body.

24. A haemostatic medical device according to claim 23, wherein the material susceptible to metabolisation within the body comprises any of the following, alone or in any combination: collagen, oxidised regenerated cellusose, poly lactic acid, poly glycolic acid, chitin, chitosan, gelatine and hyaluronic acid.

25. A haemostatic medical device according to claim 1, wherein the receptacle is generally square, rectangular, circular or elliptical.

26. A haemostatic medical device according to claim 1, wherein the receptacle comprises a tube, sphere, cone, cube, pyramid, horse shoe, or torus.

27. A haemostatic medical device according to claim 1, wherein the receptacle has a projection or protrusion for placement within a hole, cavity or orifice.

28. A haemostatic medical device according to claim 1, wherein the receptacle is formed from a material having a thickness of between around 10 µm and around 100 µm.

29. A haemostatic medical device according to claim 1, wherein the receptacle is apertured.

30. A haemostatic medical device according to claim 1, wherein the receptacle itself comprises a therapeutically active component.

31. A haemostatic medical device according to claim 1, wherein the haemostatic agent is a particulate material.

32. A haemostatic medical device according to claim 1, wherein the haemostatic agent is selected from a liquid, solution, gel, emulsion, foam or fibrous material.

33. A haemostatic medical device according to claim 1, wherein the haemostatic agent comprises a chitosan salt.

34. A haemostatic medical device according to claim 33, wherein the chitosan salt is selected from any of the following either alone or in combination: acetate, lactate, succinnate, malate, sulphate and acrylate.

35. A haemostatic medical device according to claim 33, wherein the chitosan salt constitutes at least around 5% by weight of the haemostatic agent.

36. A haemostatic medical device according to claim 35, wherein the chitosan salt constitutes at least around 20% by weight of the haemostatic agent.

37. A haemostatic medical device according to claim 33, wherein the chitosan salt is a particulate material.

38. A haemostatic medical device according to claim 37, wherein the chitosan salt has a particle size such that it will pass through a 5 mesh screen but be retained by a 80 mesh screen.

39. A haemostatic medical device according to claim 38, wherein the chitosan salt has a particle size such that it will pass through a 20 mesh screen but be retained by a 50 mesh screen.

40. A haemostatic medical device according to claim 1, wherein the haemostatic agent further comprises an inert material.

41. A haemostatic medical device according to claim 40, wherein the inert material is selected from any of the following either alone or in combination: cellulose, fumed silica, sand, clay, alginate, micro crystalline cellulose, oxidized regenerated cellulose, polyethylglycol, guar gum, xanthan gum, chitosan, chitosan derivatives, chitin, sucrose, lactose, pectin, carboxy methyl cellulose, ground corn meal, collagen, gelatine, poly vinyl alcohol, acrylic acid, poly acrylic acid polymers, barium sulphate, clay, lactose, sucrose and starch.

42. A haemostatic medical device according to claim 40, wherein the inert material constitutes at least around 30% by weight of the haemostatic agent.

43. A haemostatic medical device according to claim 40, wherein the inert material is a particulate material having a particle size approximating to the size of particles of the chitosan salt.

44. A haemostatic medical device according to claim 1, wherein the haemostatic agent comprises at least one medical surfactant.

45. A haemostatic medical device according to claim 44, wherein the medical surfactant is selected from any of the following either alone or in combination: block copolymers based on ethylene oxide and propylene oxide; fatty acids; fatty acid salts; silicone based surfactants; and emulsifiers.

46. A haemostatic medical device according to claim 44, wherein the medical surfactant constitutes from around 0.001% to around 10% by weight of the haemostatic agent.

47. A haemostatic medical device according to claim 46, wherein the medical surfactant constitutes from around 0.5% to around 1% by weight of the haemostatic agent.

48. A haemostatic medical device according to claim 33, wherein the haemostatic agent has a pH of from around 3.5 to around 6.

49. A haemostatic medical device according to claim 1, wherein the haemostatic agent is selected from any of the following either alone or in any combination: chitosan salts, starch-based haemostats, collagen powders, gelatin powders, superabsorbents, acrylic-based polymers, cationic materials, oxidised regenerated cellulose, alginate, Factor VIII, thrombin, fibrinogen, calcium, and vitamin K.

50. A method of manufacturing a medical or haemostatic device comprising the steps of:
   introducing a flowable therapeutic agent into a flexible receptacle, the flexible receptacle having a configuration selected from the group consisting of a bag, a pouch, and a sachet, at least a part of said receptacle being formed of a water-soluble or water-dispersible material, the flexible receptacle having an outer wall which is configured and arranged to overlie the physiological wound site, conform to a contour of the physiological wound site and make contact with bodily fluids, water or aqueous fluids present at the physiological target wound site; and
   containing the therapeutic agent within the flexible receptacle;
   wherein said flowable haemostatic agent is capable of being delivered to the physiological wound site upon the dissolution or dispersion of the outer wall as a result of contact with the bodily fluids, water or aqueous fluids.

51. A method according to claim 50, wherein a sheet of flexible material is longitudinally sealed to form a tube which is then filled with the therapeutic agent and transversely sealed at both ends to contain said therapeutic agent.

52. A method according to claim 50, wherein a sheet of flexible material is longitudinally sealed to form a tube which is then is sealed at a first end before introduction of the therapeutic agent and subsequent sealing at a second end to contain the therapeutic agent.

53. A method according to claim 51, wherein sealing is effected by any of the following either alone or in combination: heat, pressure, ultrasonics, moisture, and adhesive.

54. A method according to claim 50, wherein the method includes a sterilisation step.

55. A method according to claim 50, wherein the method is carried out in an environment of controlled moisture and/or temperature.

56. A method of delivering a flowable therapeutic agent to a physiological target site, comprising the steps of:
   providing a medical device comprising a flexible receptacle containing said flowable therapeutic agent, the flexible receptacle having a configuration selected from the group consisting of a bag, a pouch, and a sachet, wherein at least a part of the receptacle is formed of a water-soluble or water-dispersible material, the flexible receptacle having an outer wall which is configured and arranged to overlie the physiological wound site, conform to a contour of the physiological wound site and make contact with bodily fluids, water or aqueous fluids present at the physiological target wound site; and
   placing the medical device at the physiological target site for a sufficient time to effect treatment;
   wherein said flowable haemostatic agent is capable of being delivered to the physiological wound site upon the dissolution or dispersion of the outer wall as a result of contact with the bodily fluids, water or aqueous fluids.

* * * * *